(12) United States Patent
Kress

(10) Patent No.: US 8,262,561 B2
(45) Date of Patent: Sep. 11, 2012

(54) HYGIENE PROTECTION FOR ENDOSCOPES

(76) Inventor: Jürgen Kress, Essenbach (DE)

( * ) Notice: Subject to any disclaimer, the term of this patent is extended or adjusted under 35 U.S.C. 154(b) by 0 days.

(21) Appl. No.: 10/541,297

(22) PCT Filed: Dec. 5, 2003

(86) PCT No.: PCT/DE03/04017
§ 371 (c)(1),
(2), (4) Date: Jun. 30, 2005

(87) PCT Pub. No.: WO2004/060149
PCT Pub. Date: Jul. 22, 2004

(65) Prior Publication Data
US 2006/0052662 A1  Mar. 9, 2006

(30) Foreign Application Priority Data

Jan. 3, 2003 (DE) .............................. 203 00 037 U
May 13, 2003 (DE) ................................. 103 21 313
Oct. 31, 2003 (DE) .............................. 203 16 892 U

(51) Int. Cl.
*A61B 1/04* (2006.01)
*A61B 1/00* (2006.01)
*A61B 1/12* (2006.01)

(52) U.S. Cl. .......................... 600/121; 600/114; 600/156

(58) Field of Classification Search ................. 600/119, 600/127, 129, 153, 156, 155, 157, 186, 114, 600/158, 121–125, 128
See application file for complete search history.

(56) References Cited

U.S. PATENT DOCUMENTS

| 4,646,722 | A | * | 3/1987 | Silverstein et al. ........... 600/104 |
| 4,741,326 | A | * | 5/1988 | Sidall et al. ................... 600/123 |
| 4,886,049 | A | * | 12/1989 | Darras .......................... 600/124 |
| 4,972,825 | A | * | 11/1990 | Vescovo, Jr. .................. 600/186 |
| 4,991,564 | A | * | 2/1991 | Takahashi et al. ............. 600/124 |
| 5,217,001 | A | * | 6/1993 | Nakao et al. ....................... 128/4 |
| 5,433,221 | A | * | 7/1995 | Adair ............................ 128/849 |
| 5,518,501 | A | * | 5/1996 | Oneda et al. ................... 600/127 |
| 5,630,782 | A | * | 5/1997 | Adair ............................ 600/133 |
| 5,630,795 | A | * | 5/1997 | Kuramoto et al. .............. 604/30 |
| 5,823,191 | A | * | 10/1998 | Cho ............................... 128/844 |
| 5,944,654 | A | * | 8/1999 | Crawford ....................... 600/157 |
| 6,007,482 | A | * | 12/1999 | Madni et al. ................... 600/115 |
| 6,077,219 | A | * | 6/2000 | Viebach et al. ................ 600/114 |
| 6,258,024 | B1 | * | 7/2001 | van Der Weegen ........... 600/115 |
| 6,325,507 | B1 | * | 12/2001 | Jannard et al. ................. 351/156 |
| 7,101,358 | B2 | * | 9/2006 | Domeier et al. ............... 604/385 |
| 7,297,128 | B2 | * | 11/2007 | Binder et al. ................... 602/62 |

* cited by examiner

*Primary Examiner* — Anhtuan Nguyen
*Assistant Examiner* — Alireza Nia
(74) *Attorney, Agent, or Firm* — Edwin D. Schindler

(57) ABSTRACT

An endoscope provided with hygiene protection includes a cover, which is closed at its distal end and which is transparent for optical information, at least on the front side thereof, and which can be rolled thereon in the direction of the axis of the endoscope. The endoscope further includes one or more working channels extending in a parallel position in relation to the endoscope and terminating in an open manner on the distal end of the cover. The working channels are only connected to the distal end of the cover. There are also one or more vacuum channels having one or several openings, which terminate on the side facing away from the patient and are in addition to the one or more working channels. The working channels are positioned in between the outer side of the endoscope and the inner side of the cover. A method for adding hygiene protection to an endoscope, which includes the application of sub-atmospheric pressure between the endoscope and the cover, is also disclosed.

18 Claims, 3 Drawing Sheets

HYGIENE PROTECTION FOR ENDOSCOPES

BACKGROUND OF THE INVENTION

1. Technical Field of the Invention

Figure 1:
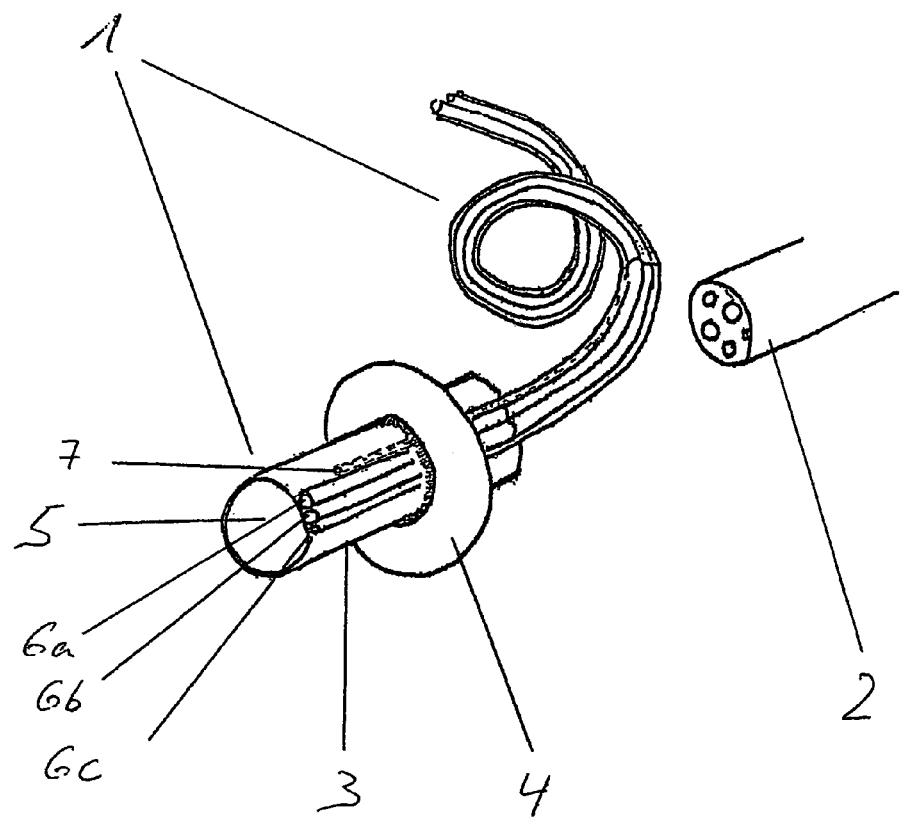

The invention relates to an endoscope with hygiene protection, which includes a cover, which is closed at the distal end thereof and which is transmissible for optical information at least on its front side, and which can be rolled on in the manner of a condom in the axial direction of the endoscope and which has one or more working channels which extend parallel to the endoscope and terminate in an open manner at the distal end of the cover. The invention further relates to a method for applying an elastic endoscope protection intended for one-off use.

2. Description of the Prior Art

Endoscopy is a diagnostic method for examining body cavities and ducts and hollow organs by direct observation by means of an endoscope. New designs of endoscopes consist of a flexible tube, in the interior of which glass fibre bundles run. The optical information from the body interior is transmitted through the glass fibres. Other endoscopes have a CCD image-converter chip, which acts as a miniaturised TV camera and makes possible output on a monitor. By means of endoscopy, tissue portions can be removed for biopsy by means of introducible forceps, loops, irrigators and suction apparatus, and relatively small operations carried out.

Since endoscopes are very expensive items of equipment, it is necessary to use them as frequently as possible to achieve a payback. To avoid contamination, unprotected endoscopes are dismantled after each use and thoroughly cleaned. The cleaning procedure includes the intensive mechanical cleansing, e.g. by brushes and the use of an ultrasonic bath. The channels extending in the interior of the endoscope are flushed after immersion in a disinfection solution by means of a pump. The entire procedure is highly time and labour intensive. In addition, the endoscope cannot be used for the period of the cleaning, so that, with an avoidable capital tie-up, additional endoscopes must be purchased to provide for the patients.

To avoid these difficulties, various disposable endoscope covers have already been proposed in, e.g., U.S. Pat. No. 4,741,326; U.S. Pat. No. 5,201,908; U.S. Pat. No. 5,217,001; and Federal Republic of Germany patent specification DE 199 18 488. Despite the evident large demand for endoscope protection covers, interestingly none of these covers has so far become established on the market.

U.S. Pat. No. 5,217,001 discloses various embodiments of an endoscope protection cover: In one of the embodiments, the cover consists of a rigid material, which, for attachment of the cover, must be pushed for its entire length over the distal tip of the endoscope. To facilitate this operation, the interior diameter of the cover is dimensioned to be bigger than the outer diameter of the endoscope. After the distal end of the endoscope lies against the distal end of the cover, that part of the cover that does not bear against the outside of the endoscope is folded back, closures being provided in the longitudinal direction, and based on the zip-lock principle, in order to fix the folded-back sleeve in the longitudinal direction. The disadvantage of this embodiment, apart from the complicated attachment of this cover, is its rigidity and the higher manufacturing costs needed for attaching the closures running in the longitudinal direction. In a further development of this endoscope protection, the cover does not have a zip lock-like closure but an airtight balloon-like cover, which lies against the inside of the cover. This balloon-like sleeve to which air can be applied, provides that the endoscope protection bears firmly against the shaft of the endoscope. The major disadvantage of this embodiment consists in the volume increase of the endoscope, since, in the interest of the patient, any volume increase of the endoscope must be avoided, since the introduction of an endoscope with a large diameter can be very painful. The somewhat rigid cover of the two aforementioned embodiments comprises tubes which run in the wall of the cover parallel to the endoscope shaft and serve as working channels.

In an alternative embodiment, U.S. Pat. No. 5,217,001, discloses an endoscope protection which can be rolled on in the manner of a condom, which, at the distal end, just like to the two first-mentioned embodiments from that document, comprise a transmissible window. Additional working channels are not provided in the endoscope protection, which can be rolled on in the manner of a condom. Its use is therefore restricted in a disadvantageous manner to optical control, and precludes the taking of biopsies.

SUMMARY OF THE INVENTION

The working channels in the endoscope protection according to the invention are connect to the distal end of the cover; in the non-distal region of the cover, the working and vacuum channels are fixed, so to speak, exposed between the endoscope shaft and the inside of the cover. In the most general case, the working channels are connected on the inside in an airtight and watertight manner only to the front face of the distal cap. The interior of the working channels is thereby only accessible from the outside of the endoscope protection.

In addition to the working channels, in the endoscope protection according to the invention, at least one vacuum channel is provided. The vacuum channel terminates in an open manner within the envelope of the endoscope protection and can have additional side openings. These side openings terminate at the inside of the cover. When a vacuum is applied to this channel, the air located between the cover and endoscope shaft is sucked out, with the consequence that the cover is drawn firmly onto the endoscope. The vacuum is maintained during the examination. This, a fixed connection between the cover and endoscope, is produced advantageously rapidly after the endoscope has been introduced comfortably into the cover, which is dimensioned somewhat larger in the interior diameter, preferably in the proximal part.

During application of the hygiene protection, one hand fixes the freely movable working channels and vacuum channels on the endoscope shaft, while the other hand rolls on the cover above the channels, which cover is rolled up in the manner of a condom or folded up as a bar.

DETAILED DESCRIPTION OF THE PREFERRED EMBODIMENTS

The gist of the invention comprises the combination of the condom-like protective cover with its own working channels, which extend outside the endoscope, the protective cover and the working channels being connected to one another in the distal region of the cover in an airtight, germ-tight and watertight manner. For attachment of the protection cover according to the invention, the distal end of the cover is pushed onto the endoscope, so that the front face, which is transmissible for optical information, is correctly positioned, i.e. positioned parallel to the distal end of the endoscope. The optical contact between the endoscope and the transparent front face of the cover is preferably produced by means of a fluid, such as, microscope immersion oil, which ideally has the same refractive index as the lens of the endoscope. During application of the endoscope protection, the channels are fixed to the endoscope with one hand, while the other hand pushes the cover, which is rolled up in the manner of a condom or folded up in the manner of a ball, over the outside of the condom, so that the cover, besides enclosing the endoscope, also encloses the working channels.

It lies within the scope of the invention that the hygiene protection is used for medical endoscopes whose diameter may be variable. Besides endoscopes for examining the esophagus and all digestive organs, endoscopes are expressly included that are used in ear, nose and throat medicine.

The cover of the endoscope according to the invention should consist of a flexible material that is airtight and watertight and is furthermore impermeable to pathological microorganisms, the same applies to the type of connection of the working channels to the cover at the distal end thereof. In general, the rubber-like materials used for medical purposes meet these requirements. Such materials have, to some extent, thermally sensitive properties, that is to say their size is reduced on heating. For the advantageous exploitation of these properties in conjunction with the endoscope according to the invention, it would be conceivable to subject the endoscope to brief heating after mounting of the protective sleeve, with or without the application of a subatmospheric pressure to the vacuum tube. In the case when the endoscope protection has the aforementioned thermally sensitive material properties, such a process step would have the advantageous effect that the endoscope protection would bear without wrinkles against the shaft of the endoscope.

In a further embodiment of the endoscope protection, it is provided that the cover can be not rolled up in the manner of a condom but be folded up in the manner of a bellows. This further development is applicable in particular when the surface of the endoscope is smooth and without projecting parts.

It lies within the scope of the invention that the internal diameter of the cover is, at least in the proximal part of the cover, slightly greater than the outer diameter of the endoscope. It is thereby advantageously possible to lay the cover against the endoscope. This is true in particular when the cover can be folded up as a bar.

Of course the cover, as a contamination protection covers at least those parts of the endoscope that are introduced into the body orifices of the patient. To avoid any contamination of the endoscope, however, the cover should be dimensioned in practice such that it also covers regions of the endoscope that do not come into contact with the patient.

In a preferred embodiment, the front face, which is transmissible to optical information, at the distal end is a transparent pane or a lens, which serves for magnification of the optical information. The optical contact between the pane or the lens and the optical channel of the endoscope is produced by a liquid, so that the optical definition is not affected. Of course, it is conceivable that the pane or the lens forms the entire surface of the front face at the distal end section. In principle, it is also conceivable that the distal end section of the cover is formed as an optically transparent cap and one or more lenses are fixed at the front face and/or laterally. The wall thickness of the cap-like end section is bigger than the wall thickness of the cover in the non-distal region. The non-distal region extends from the proximal end of the cap as far as the proximal end of the cover.

It corresponds to the teaching of the invention that the cover, which is open at the proximal end, can be fixed so as to be airtight, so that when the vacuum is applied, no air can flow in from the outside. A corresponding seal between the endoscope shaft and the sleeve can be achieved by embedding the channels lying between them in a rubber-like sleeve.

In an alternative embodiment of the cover, the latter is conically enlarged in the region of the proximal end. This facilitates the attachment of the cover and permits the additional covering of components of the endoscope that project above the endoscope shaft. Because of the wrinkle-free folding over of the cover, the latter is preferably placed under tension on the shaft and fixed by means of a chemically inert and in particular non-toxic adhesive.

For easier removal of the hygiene protection it is provided that a thread runs on the inside of the cover and over the entire length or a part of the length thereof. This thread is connected at its distal end to the cover. By pulling in a direction perpendicular to the endoscope axis, the tear thread, which acts like a cutting edge, exerts a force on the envelope that severs the latter. Such tear threads are known in principle from packaging materials.

It lies within the scope of the invention that at least one of the working channels is provided for introducing liquids or air, the channels used as such need not necessarily be stiff walled. Having rigid walls, however, is a requirement that must be made of a working channel used as a suction line. In the scope of the invention, at least one of the working channels is provided as a suction line for removing bodily fluids. Moreover at least one of the working channels is provided for guiding equipment, that is to say in particular equipment that serves for the removal of tissue samples (biopsies).

The vacuum channels essential to the invention can extend over the entire length of the endoscope cover or only over part of the cover. It is conceivable that the elastic cover is dimensioned very closely starting from the distal end as far as, for example, the first third, such that it lies closely against the endoscope shaft without the application of a vacuum. In this case, the vacuum channel will only extend over two thirds of the cover length starting from the proximal end. This region will lie completely against the endoscope shaft after application of the vacuum.

It lies within the scope of the invention that during the utilization of the endoscope a subatmospheric pressure is applied to the vacuum channel or to the vacuum channels. Because of the seal of the cover at the proximal end, however, it is not absolutely necessary for the subatmospheric pressure to be applied continually during the endoscope use.

In a further development of the endoscope according to the invention, the latter has depressions on the outside of the endoscope shaft, which extend in an axial direction. The form and depth of these depressions correspond to the diameter and profile of the working and vacuum channels, which after insertion into the depressions no longer project above the surface of the endoscope shaft. This facilitates the fixing of the channels during the application of the cover and is furthermore patient-friendly. In a further development of this embodiment it is provided that the width of the depressions in the endoscope shaft is slightly narrower than the width of the channels. Since the channels preferably consist of elastic material, for example of extensible plastic, they can be pressed into the depression on the endoscope shaft by light pressure and remain there so that they advantageously no longer need to be fixed by hand during rolling on or slipping over of the cover.

In a further development of the invention the working and vacuum channels are detachably connected to the distal end of the cover. In this case, adapter-like plug connections are recessed into the distal end region of the cover, the adapters permitting an airtight and watertight plug connection. The connection between the working channels and vacuum channels at the proximal end is naturally also airtight. It goes without saying that the adapter-like connection elements of the working channels and vacuum channels at the proximal end are compatible with the valve connections and endoscope control units which are conventional in endoscopy and familiar to the person skilled in the art. In particular, the working channels and vacuum channels should also be connectable to the endoscope control units, which are known in the prior art and only intended for one-off use. Such control units known to the person skilled in the art are preferably made of plastic.

The present invention also covers a method for attaching a disposable hygiene protection to medical endoscopes, the method being characterised by one of the following process steps:

the window at the distal end of the cover (4) is covered on the inside with a material that produces optical contact between the window and the optical channel of the endoscope (2)

the distal end of the endoscope (2) is introduced into the cover (4), which is open at the proximal end and closed at the distal end thereof the working channels (6a-6c), which are fixed at the distal end, are positioned in the depressions provided on the outside of the endoscope (2)

the cover (4), which is rolled up in the manner of a condom or folded up in the manner of bellows, is rolled on or unfolded with enclosure of the endoscope (2) and the working channels (6a to 6c)

a subatmospheric pressure is applied to the vacuum tube

If the shaft of the endoscope has no depressions on its outside, process step number 3 is not applicable

BRIEF DESCRIPTION OF THE DRAWING FIGURES

Further details and features of the endoscope protection according to the invention are explained below in greater detail with reference to examples. The illustrated example is not intended to restrict the invention, but only to explain it. In schematic view:

FIG. 1: shows the endoscope protection before fixing on the endoscope

Figure 2:
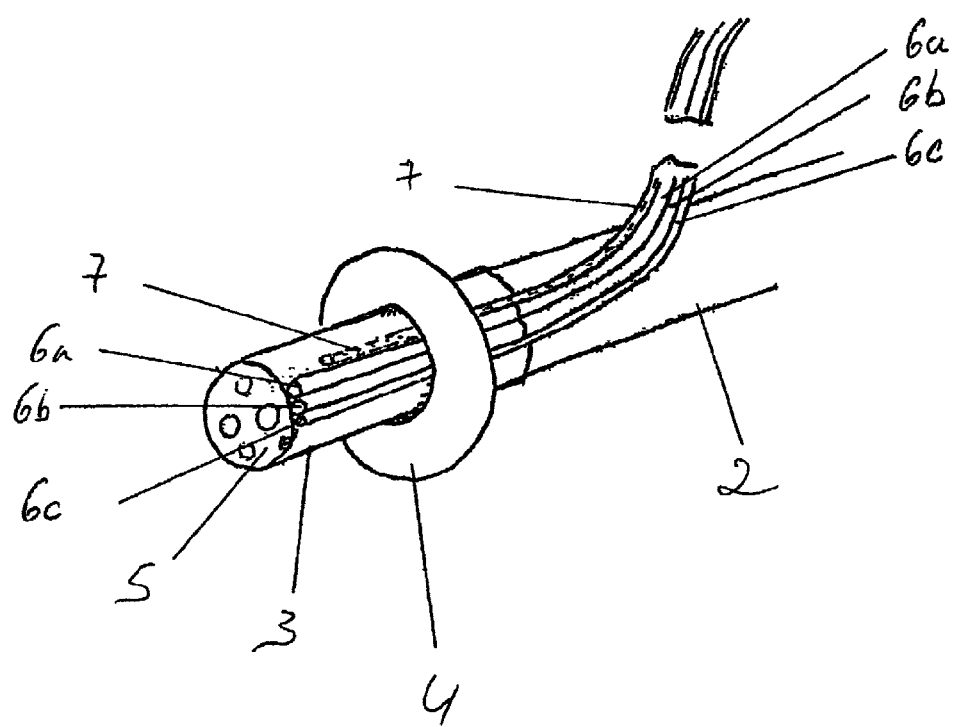
Figure 3:
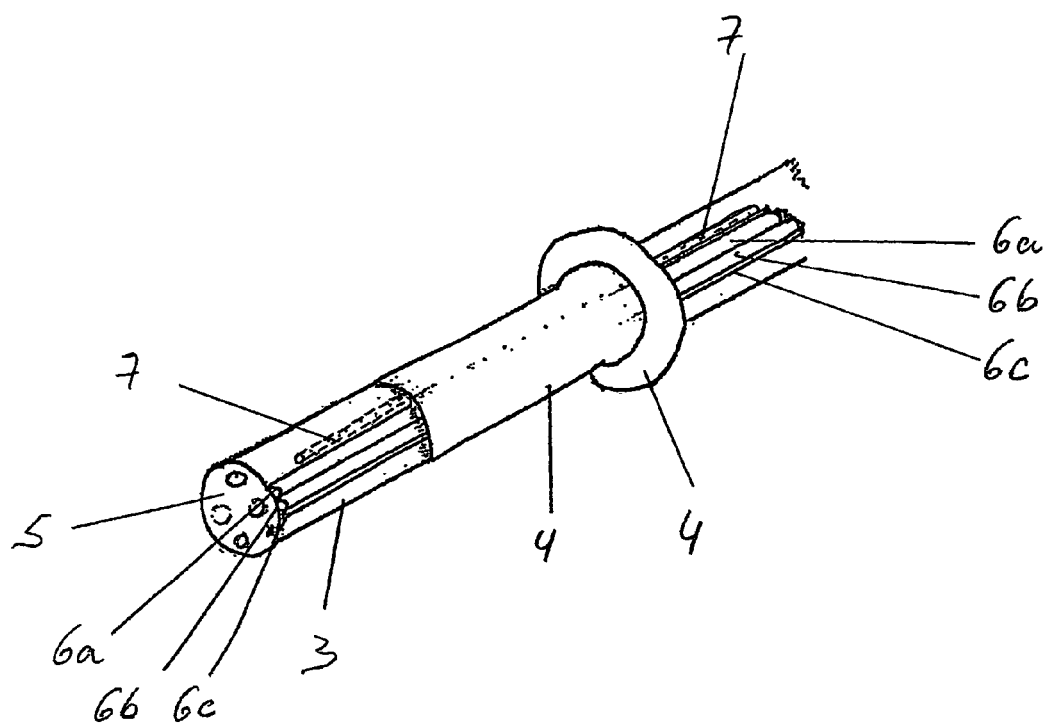

FIG. 2: shows the endoscope protection after application of the distal cap to the endoscope FIG. 3: shows the endoscope with partly rolled on endoscope protection

DETAILED DESCRIPTION OF THE DRAWING FIGURES

FIG. 1 shows the endoscope protection 1 comprising the distal end section 3 and the rolled-up cover 4, and channels 7, 6a-6c. In the illustrated example, the distal end 3 of the endoscope protection 1 is designed in the manner of a cap. At the front face 5 there is located a transparent window or a lens, which permits the transmission of optical information to the lens of the endoscope 2 without restricting the optical definition. the working channels 6a to 6c are connected to the distal end 3 of the protection cover such that the openings of the working channels 6a-6c lie on the outside of the protection cover 1. Alternatively, it would be conceivable for the working channels 6a-6c to lie against the inside of the cap-like distal end section 3 and penetrate the end section 3 at the front face 5, the end-face component of the end section 3 enclosing the working channels 6a-6c in an airtight and watertight manner.

The openly terminating vacuum channel 7 runs on the inside of the distal end section. In addition to the open end, the vacuum channel 7 can have openings that terminate at the inside of the endoscope cover 3 and 4.

In the part projecting beyond the distal end section 3, the working channels 6a-6c and the vacuum channel 7 are exposed.

FIG. 2 shows the protection cover described in FIG. 1 after the distal end section 3 of the protection cover has been pushed onto the distal end of the endoscope 2. In the illustrated state, the working channels 6a-6c and the vacuum channel 7 are still exposed in the part projecting beyond the distal end section.

FIG. 3 shows how the cover 4, which can be rolled up in the manner of a condom, after rolling on, covers the working channels 6a-6c and the vacuum channel 7, after rolling on in the direction of proximal end of the endoscope 2. The channels are fixed under the cover 4, which bears on them under tension, without further fastening on the shaft of the endoscope 2. In the illustrated example, the channels lie on the endoscope shaft. Alternatively, it is conceivable that the channels 6a-6c and 7 are recessed in a depression provided for this purpose in the endoscope 2, so that the cover 4 surrounds the endoscope 2 in the circular cross-section.

The invention claimed is:

1. An endoscope with hygiene protection, comprising:
an endoscope having a flexible tube, a lens and fibers therein;
a cover closed at a distal end and transmissible for optical information, at least on a front face of said cover, the cover being configured to be pushed onto said endoscope and capable of being rolled and unrolled in an axial direction of said endoscope, said cover including a material that is airtight, watertight and impermeable to pathological microorganisms;
said cover including its own working channel extending parallel to said endoscope and terminating in an open mode at said distal end of said cover, said working channel being connected only to said distal end of said cover and positioned between an outer surface of said endoscope and an inside of said cove, connection of said cover to said working channel to said distal end of said cover being made airtight, watertight and impermeable to pathological microorganisms; and,
said cover further consisting of only a single vacuum channel connected to means for applying sub-atmospheric pressure to said single vacuum channel during use of said endoscope, said single vacuum channel being positioned between the outer surface of said endoscope and said inside of said cover and parallel to said working channel, said single vacuum channel having at least one opening including additional side openings terminating at said inside of said cover for pressing said cover onto said endoscope via application of sub-atmospheric pressure, said single vacuum channel being a dedicated vacuum channel that is a different channel from said working channel.

2. The endoscope with hygiene protection according to claim 1, further comprising means for varying cross-sectional diameter.

3. The endoscope with hygiene protection according to claim 1, wherein said cover is flexible and elastic and foldable in the axial direction of said endoscope.

4. The endoscope with hygiene protection according to claim 1, wherein at least a portion of said cover has an internal diameter that is larger than an external diameter of said endoscope.

5. The endoscope with hygiene protection according to claim 1, further comprising a transparent pane or lens on said distal end of said cover on said front face of said cover.

6. The endoscope with hygiene protection according to claim 5, wherein said transparent pane or said lens at least partially forms said front face of said distal end of said cover.

7. The endoscope with hygiene protection according to claim 1, wherein said distal end of said cover is an optically transparent cap.

8. The endoscope with hygiene protection according to claim 7, wherein said distal end of said cover has a wall thickness that is greater than a wall thickness of a non-distal region of said cover.

9. The endoscope with hygiene protection according to claim 1, wherein said cover, when open at a proximal end, is fixable to be airtight on a shaft of said endoscope.

10. The endoscope with hygiene protection according to claim 9, wherein said cover is conically enlarged in a vicinity of said proximal end with a portion of said cover being folded backwardly to be wrinkle-free in said vicinity of said proximal end and fixable via a chemically inert and non-toxic adhesive.

11. The endoscope with hygiene protection according to claim 1, further comprising a tear thread connected to said cover at said distal end and running parallel to said endoscope on the inside of said cover.

12. The endoscope with hygiene protection according to claim 1, wherein said single vacuum channel extends for at least a portion of a length of said cover.

13. The endoscope with hygiene protection according to claim 1, further comprising depressions in an axial direction on the outer surface of said endoscope, said depressions corresponding in shape and in depth to a diameter and profile of said working channel and said single vacuum channel.

14. The endoscope with hygiene protection according to claim 13, wherein said depressions have a width, running in the axial direction on said outer surface of said endoscope, which is smaller than the width of said depressions at their center points.

15. The endoscope with hygiene protection according to claim 1, wherein said working channel and said single vacuum channel are detachably connected to said distal end of said cover.

16. The endoscope with hygiene protection according to claim 1, wherein said working channel and said single vacuum channel are fixed to said distal end of said cover.

17. A method for attaching a hygiene protection system to an endoscope, said endoscope including:
an endoscope having a flexible tube, lens and fibers therein;
a cover closed at a distal end and transmissible for optical information via a window, at least on a front face of said cover, the cover being configured to be pushed onto said endoscope and capable of being rolled in an axial direction of said endoscope;
said cover including its own working channel extending parallel to said endoscope and terminating in an open mode at said distal end of said cover, said working channel being connected only to said distal end of said cover and positioned between an outer surface of said endoscope and an inside of said cover; and,
said cover further consisting only of a single vacuum channel connected to means for applying sub-atmospheric pressure to said single vacuum channel during use of said endoscope, the single vacuum channel being positioned between the outer surface of said endoscope and said inside of said cover and parallel to said working channel, said single vacuum channel having at least one opening including additional side openings terminating at said inside of said cover for pressing said cover onto said endoscope via application of sub-atmospheric pressure, said single vacuum channel being a dedicated channel that is a different channel from said working channel,
said method comprising the steps of:
coating an inner side of said window at said distal end of said cover for producing optical contact between said window and an optical channel of said endoscope;
introducing a distal end of said endoscope into said cover, said cover being open at a proximal end and closed at said distal end thereof;
rolling said cover onto, or unfolding said cover with, an enclosure of said endoscope and said working channel; and,
applying sub-atmospheric pressure to said single vacuum channel for pressing said cover onto said endoscope.

18. A method for attaching a hygiene protection system to an endoscope, said endoscope including:
an endoscope having a flexible tube, lens and fibers therein;
a cover closed at a distal end and transmissible for optical information via a window, at least on a front face of said cover, the cover being configured to be pushed onto the endoscope and capable of being rolled in an axial direction of said endoscope;
said cover including its own working channel extending parallel to said endoscope and terminating in an open mode at said distal end of said cover, said working channel being connected only to said distal end of said cover and positioned between an outer side of said endoscope and an inside of said cover; and,
said cover further consisting only of a single vacuum channel connected to means for applying sub-atmospheric pressure to said single vacuum channel during use of said endoscope, the single vacuum channel being positioned between the outer surface of said endoscope and said inside of said cover and parallel to said working channel, said single vacuum channel having at least one opening including additional side openings terminating at said inside of said cover for pressing said cover onto said endoscope via application of sub-atmospheric pressure, said single vacuum channel being a dedicated channel that is a different channel from said working channel,
said method comprising the steps of:
coating an inner side of said window at said distal end of said cover for producing optical contact between said window and an optical channel of said endoscope;
introducing a distal end of said endoscope into said cover, said cover being open at a proximal end and closed at said distal end thereof;
fixing said working channel at said distal end of said cover, said working channel being positioned in depressions provided on an outer surface of said endoscope;
rolling said cover onto, or unfolding said cover with, an enclosure of said endoscope and said working channel; and,
applying sub-atmospheric pressure to said single vacuum channel for pressing said cover onto said endoscope.

* * * * *